United States Patent [19]

Potter

[11] 4,220,041
[45] Sep. 2, 1980

[54] ALIEN LIQUID DETECTOR AND CONTROL

[76] Inventor: Bronson M. Potter, R.F.D. 1, Mason, N.H. 03048

[21] Appl. No.: 965,899

[22] Filed: Dec. 4, 1978

Related U.S. Application Data

[63] Continuation-in-part of Ser. No. 785,347, Apr. 7, 1977, abandoned.

[51] Int. Cl.³ ............................................. G01N 25/18
[52] U.S. Cl. ................................................ 73/61.1 R
[58] Field of Search ....................... 73/53, 61.1 R, 204, 73/295

[56] References Cited

U.S. PATENT DOCUMENTS

| | | | |
|---|---|---|---|
| 3,852,997 | 12/1974 | Horvath | 73/61.1 R |
| 3,887,864 | 6/1975 | Knudsen | 323/75 H |
| 3,898,554 | 8/1975 | Knudsen | 323/75 H |
| 4,016,763 | 4/1977 | Grindheim | 323/75 H |

FOREIGN PATENT DOCUMENTS

| | | |
|---|---|---|
| 910000 | 11/1962 | United Kingdom . |
| 1192777 | 5/1970 | United Kingdom . |
| 1214266 | 12/1970 | United Kingdom . |
| 1233944 | 6/1971 | United Kingdom . |
| 1389767 | 4/1975 | United Kingdom . |
| 1396462 | 6/1975 | United Kingdom . |
| 1454794 | 11/1976 | United Kingdom . |
| 1458447 | 12/1976 | United Kingdom . |

Primary Examiner—Gerald Goldberg
Assistant Examiner—Joseph W. Roskos

[57] ABSTRACT

An alien liquid detector employs a monitoring element and an energizing circuit for maintaining the temperature of the monitoring element substantially above ambient temperature. For this purpose an electronic circuit controls a flow of heating current to the monitoring element. The presence of an alien liquid is detected by sensing a predetermined change in heating current flow to the monitoring element, e.g., to distinguish between water and oil.

In preferred embodiments the monitoring element is a thermistor whose resistance is compared with a reference resistance and heating current through the thermistor is controlled in accordance with the difference. In one embodiment a bridge circuit senses the resistance difference; the difference may be sensed by an operational amplifier arrangement. Features of the invention include positioning the monitoring element at the surface of water, slightly immersed, so that the power required to maintain the thermistor temperature substantially above ambient temperature serves to detect presence of oil pollution at the surface.

18 Claims, 9 Drawing Figures

ALIEN LIQUID DETECTOR AND CONTROL

This is a continuation-in-part of application Ser. No. 785,347 filed Apr. 7, 1977, now abandoned.

This invention relates to devices for sensing the presence of an alien immiscible liquid for purposes such as detecting oil spills on water.

The purpose of the invention is to provide devices having several advantages over alternative techniques. The invention enables devices to be simple, durable, and to be made at low cost. Moreover, the devices can be extremely sensitive so that liquids difficult to discriminate from water, for example, may be reliably detected.

According to the invention, the device which accomplishes these objects comprises a monitoring element exposed for heat transfer contact with an alien immiscible liquid when present on a desired liquid, the monitoring element having an electrical characteristic that changes as a single-valued function of temperature. An electronic circuit responsive to change in said characteristic of the monitoring element controls the flow of heating current to the element to establish the temperature of the element substantially above ambient temperature, e.g., at least about 20° F. (10° C.) above ambient, preferably below the boiling point of water. The circuit includes reference means representing a predetermined desired value for said electrical characteristic of the monitoring element. The electronic circuit is adapted, upon said change in the actual value of said electrical characteristic of the monitoring element, to change the heating current flow to the monitoring element to restore said actual value of said characteristic of the monitoring element toward said predetermined desired value. An indicator responsive to a predetermined change in the heating current flow to the monitoring element indicates the presence of the alien liquid.

Preferred embodiments of the invention feature a resistance comparator signalling the difference between the present resistance value of a thermistor and a reference, and a power regulator responsive to the comparator to vary the flow of heating current through the thermistor to reduce the resistance difference.

In one such embodiment the resistance comparator preferably comprises at least one reference resistor and a transistor means connected so that the signal on an output lead of the transistor means represents the resistance difference. The power regulator preferably comprises a transistor means operative as a series regulator connected between an energy source and the thermistor. The output lead of the resistance comparator is connected to the effective base of the power regulator transistor means, thereby controlling the flow of heating current through the thermistor.

In particular embodiments the thermistor and a plurality of resistors comprise a bridge network connected to a resistance comparator means to signal the degree of unbalance of the bridge network attributable to the difference between the present thermistor resistance value and the predetermined null value. Specifically, the bridge network comprises a first resistor having a resistance value equal to the predetermined null value, and a pair of series-connected resistors of equal value comprising a divider. The divider forms one path from the power regulator to ground and the first resistor and thermistor, connected in series, form a second path from the power regulator to the ground. The resistance comparator means has a first input effectively connected to the mid-point of the divider, and a second input effectively connected between the first resistor and the thermistor. Its effective output is connected to control the power regulator. The indicator preferably is a threshold device that may monitor the voltage applied to the bridge network or the current flow through the thermistor for example, and that produces an output in response to a sensed change in heating current flow from a predetermined reference value. With a thermistor that has a negative temperature coefficient, i.e. thermistor resistance decreases as its temperature rises, a comparator transistor may have its base effectively connected to the midpoint of the divider, its emitter effectively connected between the first resistor and the thermistor and its collector effectively connected to control the power register. A thermistor having a positive temperature coefficient may also be used, and in such case, the thermistor may be connected between the effective emitter of a resistance comparator transistor means and the power regulator. A diode is preferably included in either case in a position to compensate for the forward potential between the base and emitter of the resistance comparator transistor means. These embodiments also include indicator means responsive to a predetermined change in the voltage across the bridge, this voltage being interdependent with the current through the thermistor.

In other embodiments employing the above-mentioned comparator and power regulator arrangement, a thermistor and a reference resistor are connected in series in an electronic energizing circuit so that the same value of current flows through each of them. In one such embodiment one input of an operational amplifier is connected to the junction between the thermistor and the reference resistor and a second operational amplifier input is connected to the junction between a matched pair of series connected resistors that are connected in parallel with the thermistor-reference resistor. The operational amplifier output is connected to the junction between the pair of matched resistors and regulates the flow of heating current through the thermistor in a manner tending to maintain the resistance of the thermistor equal to the resistance value of the reference resistor. The operational amplifier output is also monitored by a threshold circuit whose output indicated the presence of an alien liquid. In another embodiment, connected across the thermistor and reference resistor are the inputs to separate operational amplifier means whose outputs are measures of the voltages across the thermistor and reference resistor. Since the current flow through the thermistor equals that through the reference resistor, the outputs of the operational amplifier means also indicate the resistance values of the thermistor and reference resistor. A further operational amplifier means is disposed in the circuit so that its input is the difference between the outputs of the operational amplifier means whose inputs are connected across the thermistor and reference resistor. The output of this further operational amplifier means, proportional to the difference in resistance between the thermistor and the reference resistor, constitutes the comparator output and is connected to a transistor means operative as a series regulator which regulates the heating current flow through the thermistor in a manner tending to maintain the resistance of the thermistor equal to the resistance value of the reference resistor. An indicator responsive to a predetermined change in the heating current flow to the thermistor indicates the presence of the alien liquid.

The preferred embodiments of the invention are detectors for sensing the presence of an alien liquid on the surface of a body of water. In such an embodiment, the detector circuit is incorporated into a probe for positioning the thermistor at the surface of water that may be contaminated, the probe supported e.g. by a float on the surface of the water or by a suspension system. When the water surface is contaminated by a fluid whose viscosity is lower than that of water, such as high petroleum distillates, and when the thermistor has a negative temperature coefficient, the heating effect of the thermistor upon the unknown fluid is less than when water alone is present thereby utilizing reduced convection heat loss to detect the alien liquid.

A further embodiment of the invention is a detector comprising a thermistor circuit described above and a reference, including a means for producing a signal representing the difference between the output signal of the thermistor circuit and the reference. In one embodiment, the reference comprises an adjustable resistor through which current flows. In another embodiment, the reference comprises a second thermistor circuit, one thermistor being exposed to a reference liquid and the other thermistor to an environment at the same temperature as the reference liquid, whose heat transfer conditions, e.g., specific heat, may vary from those of the reference liquid. Means are provided to produce a signal representing the difference between the output signals of the two thermistor circuits. When this embodiment is employed as an oil detector, the reference thermistor is exposed to water and the thermistor of the other circuit is exposed to fluid which may be oil or water. A predetermined difference output indicates the presence of oil.

In a still further embodiment of the invention herein, the thermistor circuit consists of a constant current circuit having two parallel branches, one branch containing a thermistor, and the other connected through the collector and emitter of a transistor means, the base of the transistor means connected in a feedback relation to respond to the voltage change across the thermistor.

The embodiments and features of the invention herein will be further understood in conjunction with the following drawings in which.

DESCRIPTION OF THE PARTICULAR EMBODIMENTS

Figure 1:
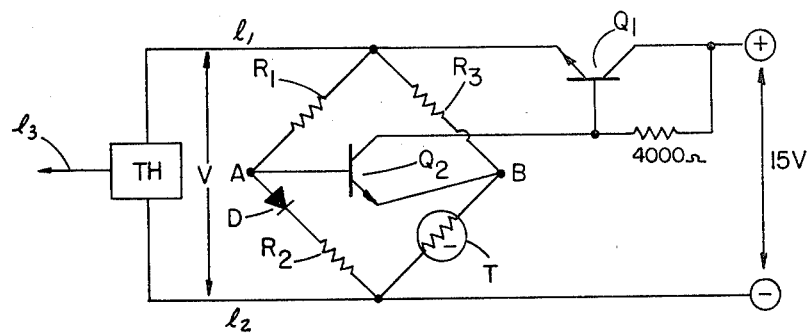
FIG. 1 is a schematic diagram of the circuitry of a preferred embodiment according to the invention employing a negative temperature coefficient thermistor.

Referring to FIG. 1, transistor $Q_1$, a five-watt silicon transistor with $\beta$ over 100, operates as a standard series regulator. Transistor $Q_2$, a standard NPN entertainment transistor with $\beta$ over 100, serves to modify transistor $Q_1$'s base current in response to the current flow between the base and emitter of transistor $Q_2$, caused in turn by a resistance imbalance in the bridge circuit shown. Two arms of the bridge are formed by 1000 $\Omega$ resistors $R_1$ and $R_2$; the other arms are formed by a 470 $\Omega$ reference resistor $R_3$ and a thermistor T, Fenwal GD31SM2, having a negative temperature coefficient. The base and emitter of transistor $Q_2$ are connected to the midpoints of this bridge circuit. The diode D is a standard 100 milliwatt device which compensates for the forward potential between the base and emitter of transistor $Q_2$. At 25° C. ambient temperature conditions, the thermistor T has a resistance of 1000 $\Omega$.

When the circuit is activated, a potential difference develops between points A and B of the bridge circuit, because the initial thermistor resistance, 1000 $\Omega$, does not match the resistance of the 470 $\Omega$ reference resistor $R_3$. Because of this potential, transistor $Q_2$ is turned off allowing transistor $Q_1$ to be fully on. Power, therefore, flows through the thermistor to ground causing the thermistor to be heated. Since this thermistor has a negative temperature coefficient, as it heats, its resistance begins to drop. As the thermistor approaches 50° C. in temperature, its resistance approaches 470 $\Omega$, the value of its companion reference resistor $R_3$, the potential difference between points A and B drops as the bridge becomes balanced, and transistor $Q_2$ begins to turn on, robbing transistor $Q_1$ of some of its base current, thereby turning it partly off. As transistor $Q_1$ progressively turns off, the current flow through the thermistor is reduced. This electronic negative feedback circuit, therefore, attempts to maintain the thermistor resistance equal to the resistance of the reference resistor in the face of changing conditions in the surrounding medium. The total system is stable and the thermistor resistance is driven to the reference resistance without overshoot or hunting. If, for example, conditions in the surrounding medium change in a way tending to reduce thermal transfer from the thermistor, the thermistor temperature will rise, the bridge will become unbalanced, transistor $Q_2$ turns more on, and transistor $Q_1$ supplies less power to the thermistor, allowing the thermistor to cool and changing its resistance value toward that of the reference resistor. A threshold circuit TH moniters the voltage V on output leads $l_1$ and $l_2$ as an indication of the current flow through the thermistor, and produces an output on $l_3$ when a predetermined change in the voltage V is sensed.

Figure 2:
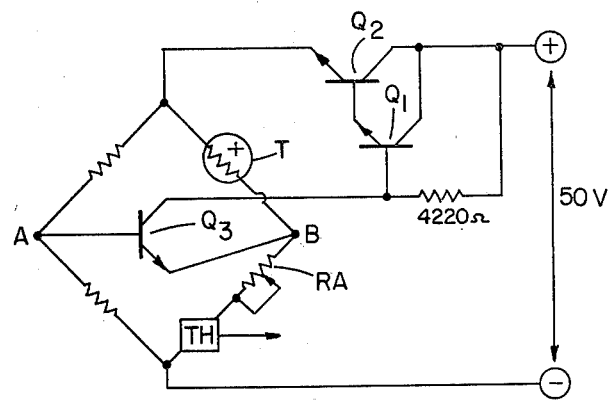
FIG. 2 is a schematic diagram similar to FIG. 1 of an embodiment of the invention employing a positive temperature coefficient thermistor.

The similar embodiment shown in FIG. 2 employs a positive temperature coefficient thermistor. The position of the thermistor and its reference resistor, an adjustable resistor $R_a$ set e.g., at 560 $\Omega$ in this case, are reversed from the arrangement in FIG. 1. The other arms of the bridge comprise resistors of 1330 $\Omega$. The power regulation portion of this circuit consists of two transistors, $Q_1$ and $Q_2$, connected in a Darlington configuration allowing higher gain than the single transistor $Q_1$ of FIG. 1, and hence tighter regulation of the thermistor's resistance. This circuit operates in much the same way as the circuit of FIG. 1, except that at ambient conditions the thermistor's resistance will be lower than its reference resistor. When the circuit is activated, the bridge will be unbalanced; that is, there will be a potential difference between points A and B. Transistor $Q_3$ will be turned off, allowing transistors $Q_1$ and $Q_2$ to supply current to the thermistor, heating it, and increasing its resistance. When this resistance reaches the set resistance of 560 $\Omega$, transistor $Q_3$ turns on, and transistors $Q_1$ and $Q_2$ reduce the power flow to the thermistor. In this way, the thermistor resistance is maintained equal to its reference or null resistance. As with the circuit of FIG. 1, this circuit is stable with no overshoot or hunting as the thermistor resistance approaches the resistance of the reference resistor. Threshold circuit TH connected between the reference resistor and ground, monitors the current through the thermistor and provides an output indication on sensing a predetermined change in heat transfer from the thermistor to the surrounding medium.

Figure 3:
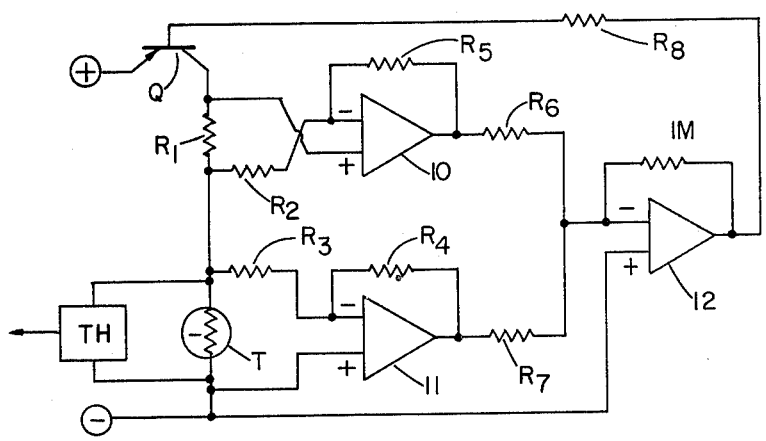
FIGS. 3 and 3a are schematic diagrams of embodiments of the invention employing operational amplifiers.

FIG. 3 is an embodiment of the invention embodying operational amplifiers. Operational amplifier 10 is connected across reference resistor $R_1$ and serves as a gain of one inverter amplifier, with its output proportional to the voltage across resistor $R_1$. Operational amplifier 11 is connected across the thermistor T and serves as a gain of one amplifier, with its output proportional to the voltage across thermistor T. The two outputs are electrically subtracted and the difference serves as the input to operational amplifier 12, which serves as a gain of ten summing amplifier, with its output proportional to the difference in the voltages across the thermistor T and reference resistor $R_1$. Because the current through thermistor T equals that through reference resistor $R_1$, the output of operational amplifier 12 is proportional to the difference in resistance between thermistor and reference resistor. This output signal from operational amplifier 12 is connected to the base of transistor Q thereby controlling the flow of power through thermistor T and regulating its resistance. A predetermined change in the amount of power required to maintain the resistance of thermistor T equal to the resistance of resistor $R_1$ triggers threshold circuit TH connected across the thermistor.

In this embodiment the frequency compensation and power supply connections to the operational amplifiers (routine to the art) are now shown. The following components are used:

| thermistor T | Fenwal GD25SM2 |
| --- | --- |
| series regulator Q | 2N1038 |
| operational amplifiers 10, 11, 12 | 709 |
| resistances: | |
| $R_1$ | 33 $\Omega$ |
| $R_2$ | 2.7 K $\Omega$ |
| $R_3$ | 2.7 K $\Omega$ |
| $R_4$ | 2.7 K $\Omega$ |
| $R_5$ | 2.7 K $\Omega$ |
| $R_6$ | 10 K $\Omega$ |
| $R_7$ | 10 K $\Omega$ |
| $R_8$ | 330 $\Omega$ |

The sensitivity of such a system is shown by the following table which displays the voltage, current, and power levels required to maintain the resistance of this thermistor at about 50 $\Omega$ when immersed in air, kerosene, and water.

| | Voltage | Current | Power |
| --- | --- | --- | --- |
| Air | 1V | 20 ma | 20 mw |
| Kerosene | 3V | 60 ma | 180 mw |
| Water | 5V | 100 ma | 500 mw |

In another embodiment of the operational amplifier type, the non-inverting gain-of-one operational amplifier can be eliminated at the expense of extremely small matching error between thermistor potential and following operational amplifier. This permits using an integrated circuit in which two operational amplifiers and associated circuits for frequency compensation lie on one chip and the need for external frequency compensation is eliminated.

Figure 3A:
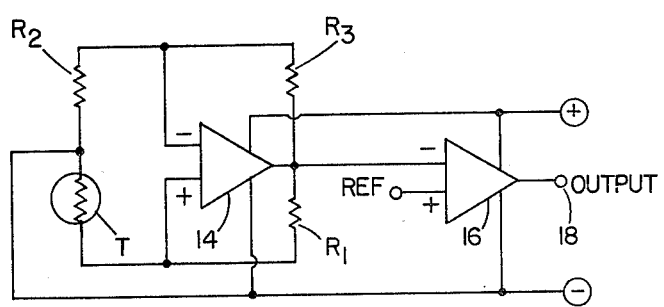

FIG. 3a shows another operational amplifier embodiment in which operational amplifier 14 has one input connected to the junction between 250 $\Omega$ reference resistor $R_1$ and thermistor T (GD25SM2) and another input connected to the junction between 2K $\Omega$ resistors $R_2$ and $R_3$. The output of amplifier 14 is connected to the junction between resistors $R_1$ and $R_3$ and changes the voltage at that junction as a function of relative change in the voltages applied to its inputs. That change in output voltage is monitored by threshold senser operational amplifier 16 and amplifier 16 produces an alien liquid indication signal at terminal 18 when the output voltage of amplifier 14 reverses polarity with respect to the reference threshold (REF).

Figure 4:
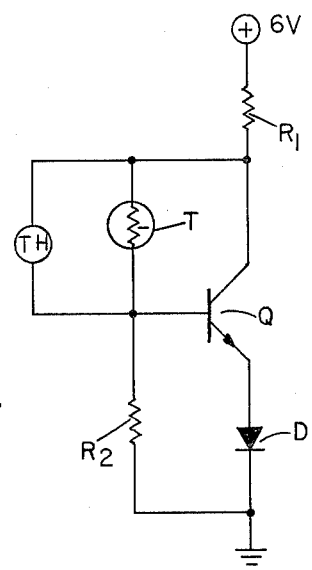
FIG. 4 is a schematic diagram of an embodiment of the invention employing a constant current circuit and a negative temperature coefficient thermistor.
Figure 5:
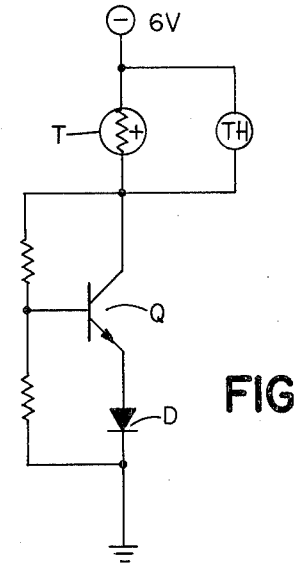
FIG. 5 is a schematic diagram of an embodiment similar to FIG. 4 employing a positive temperature coefficient thermistor.

FIG. 4 is an embodiment of the invention employing a constant current circuit which attempts to maintain a constant current flow through collector resistor $R_1$. There are two parallel paths for current to flow from the energy source to ground, one through transistor Q and diode D and the other through thermistor T and $R_2$. Thermistor T is connected between the base and collector of transistor Q enabling transistor Q to control the flow of current through thermistor T. The component values are chosen so that the circuit keeps current through T constant thereby tending to restore a predetermined resistance value, however imperfectly. If thermistor T becomes immersed in an alien liquid such that thermistor T heats, for example, its resistance decreases causing the potential at the base of transistor Q to rise, progressively turning transistor Q on, thereby allowing less current to flow through the thermistor T. This reduced power through thermistor T cools it, causing its resistance to increase. Threshold circuit TH senses the voltage across the thermistor and provides an output in response to a predetermined change in the heat transfer from the thermistor to the surrounding medium. FIG. 5 is a schematic diagram showing means of accomplishing similar results with a positive temperature coefficient thermistor.

Figure 6:
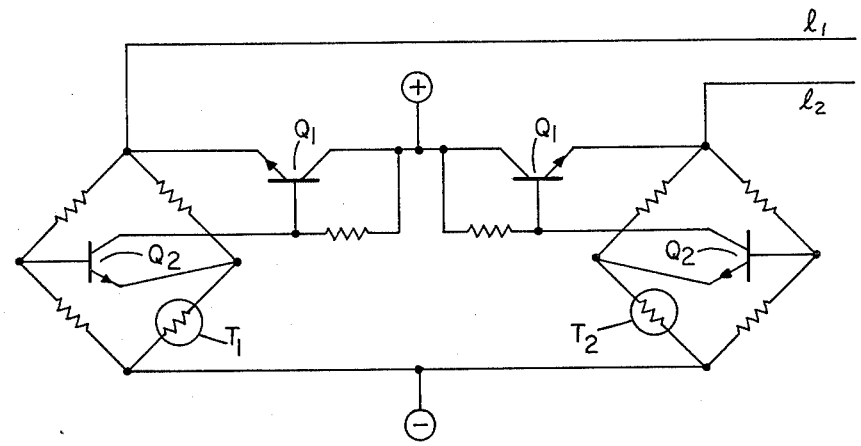
FIG. 6 is a schematic diagram of circuitry combining two of the thermistor circuits of FIG. 1 in a summing arrangement.

Referring to FIG. 6, two of the circuits of FIG. 1 are shown connected in a summing arrangement. One of the thermistor circuits acts as a reference. Whenever the power flow through thermistor $T_1$ differs from the power flow through thermistor $T_2$, an output signal develops on leads $l_1$ and $l_2$. If, for example, thermistor $T_2$, the reference, is exposed to water, and thermistor $T_1$ is exposed to water with a small amount of alcohol added, the power required to maintain the two thermistors at a constant, preselected temperature will differ because of the different heat transfer characteristics of the two liquids. An output signal will therefore develop on leads $l_1$ and $l_2$ which triggers threshold circuit TH to indicate the presence of an adulterant. For certain applications the reference circuit need not be another thermistor circuit; it may consist of a simple resistance circuit to serve as a reference.

Figure 7:
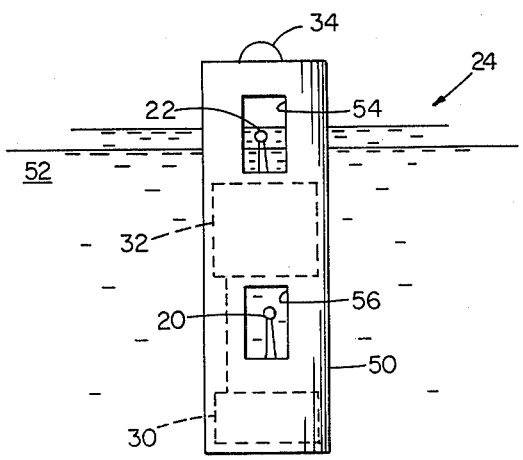
FIG. 7 is a diagrammatic view of an oil detection unit employing the circuitry of FIG. 6.

FIG. 7 shows the invention embodied as an oil detection unit employing the summing circuit of FIG. 6. The oil detection system includes a buoyant, tubular housing 50 designed to float on water 52 to be monitored. Housing 50 has upper and lower recesses 54, 56. The buoyancy of housing 50 is such that recess 54 is disposed at the surface of the water and recess 56 is submerged. Reference thermistor 20 is disposed in recess 56 so that it remains under water. Monitoring thermistor 22 is disposed in recess 54 at the air-liquid interface so that it is exposed to oil should a film of oil 24 exist on the monitored surface. The oil detection unit may be self-contained and include batteries 30 (which function as ballast), the electronic circuit of FIG. 6, 32, and an output indicator 34 on its upper surface. In another embodiment, the unit may be connected by flexible cable (not shown) to a remote power supply and to remote output indicator circuitry.

Figure 8:
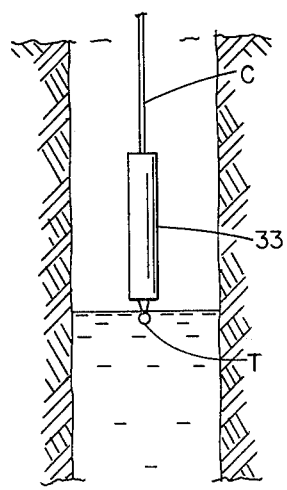
FIG. 8 is a diagrammatic view of a suspended probe unit.

In the cable-suspended detector of FIG. 8, the thermistor T at the end of the suspension cable C is exposed to contact the fluid medium for instance in a bore in the ground. The thermistor is connected to the comparator 33 as shown in FIG. 1 and supplies its output along leads incorporated in the suspension cable.

While the preferred devices used to perform the thermistor functions of this invention are those semiconductor units sold as "thermistors", it will be understood that certain of the advantages of the invention can be obtained using other devices, or combinations whose effects upon the circuit varies with temperature in single-valued relation. For instance, a temperature-sensitive diode may be employed in certain instances, provided its temperature characteristic corresponds to the needs of the particular application involved.

What is claimed is:

1. A detector for detecting an alien immiscible liquid in the presence of a desired liquid, e.g., for detecting oil pollution at a surface boundary of water, comprising a monitoring element exposed for heat transfer contact with said alien liquid when present, said monitoring element having an electrical characteristic that changes as a single-valued function of temperature, an electronic circuit to control the flow of heating current to said element to establish the temperature of said element at a value substantially above ambient temperature, said circuit including reference means representing a predetermined desired value for said electrical characteristic of said monitoring element and being adapted, upon change in the actual value of said electrical characteristic of said monitoring element, to change said heating current flow to said monitoring element to restore the value of said characteristic toward said predetermined desired value, and an alien liquid indicator circuit responsive to a predetermined change in said heating current flow to said monitoring element for indicating the presence of said alien liquid, said predetermined change related to the difference in the specific heats of the alien and the desired liquids.

2. The detector of claim 1 characterized in that said monitoring element is a thermistor.

3. The detector of claim 1 characterized in that said electrical characteristic is resistance and said electronic circuit includes a resistance comparator signalling the difference between the present resistance value of said monitoring element and said desired value, and a current regulator responsive to said comparator to vary said heating current flow through said element to reduce said difference.

4. The detector of claim 3 wherein said regulator comprises a transistor means operative as a series regulator, connected between an energy source and said thermistor.

5. The detector of claim 3 wherein said resistance comparator and said current regulator comprise operational amplifier means.

6. The detector of claim 3 wherein said resistance comparator comprises first, second, and third operational amplifier means, the first connected so that its output represents the desired resistance value, the second connected so that its output represents the resistance value of said monitoring element and said third operational amplifier means having as inputs said outputs of said first and second operational amplifier means, and connected so that the output of said third operational amplifier means represents said difference between the present resistance value of said element and said desired value.

7. The detector of claim 3 wherein said resistance comparator comprises at least one reference resistor and a transistor means connected so that the signal on an output lead of said transistor means represents said difference.

8. The detector of claim 1 wherein said monitoring element and a plurality of resistors comprise a bridge network, and said electronic circuit includes a resistance comparator connected to signal the degree of unbalance of said bridge network attributable to the difference of the present resistance value of said monitoring element from said predetermined desired value.

9. The detector of claim 8 wherein said monitoring element is a thermistor, said bridge network comprises a first resistor having a resistance value equal to said predetermined desired value, and a pair of series connected resistors comprising a divider, said divider forming one path to ground and said first resistor and said thermistor connected in series forming a second path in parallel to said first path to ground, said resistance comparator having a first input effectively connected to the midpoint of said divider and a second input effectively connected between said first resistor and said thermistor and an output connected to control the flow of current through said parallel first and second paths.

10. The detector of claim 9 wherein said resistance comparator comprises operational amplifier means that has an output connected to supply current through said parallel first and second paths.

11. The detector of claim 9 wherein said resistance comparator comprises a transistor means connected so that the signal on an output lead of said transistor means represents said difference.

12. The detector of claim 11 wherein a diode is included in said divider in a position to compensate for forward potential between base and emitter.

13. The detector of claim 1 in the form of a constant current type circuit having two parallel branches, one branch containing said monitoring element and the other connected through the collector and emitter of a transistor means, the base of said transistor means connected in feedback relation to respond to voltage change across said monitoring element.

14. The detector of claim 1 characterized in that said monitoring element is incorporated in a probe for positioning said monitoring element at the surface of said desired liquid.

15. The detector of claim 14 wherein said probe comprises a float adapted to freely float upon the surface of said liquid.

16. A detector for detecting an alien immiscible liquid in the presence of a desired liquid, e.g., for detecting oil pollution at a surface boundary of water, comprising a detection circuit having a thermistor exposed for heat transfer contact with said alien liquid when present, said thermistor having an electrical characteristic that changes as a single-valued function of temperature, an electronic circuit to control the flow of heating current to said thermistor to establish the temperature of said thermistor at a value substantially above ambient temperature, said circuit including reference means representing a predetermined desired value for said electrical characteristic of said thermistor and being adapted, upon change in the actual value of said electrical characteristic of said thermistor, to change said heating current flow to said thermistor to restore the value of said characteristic toward said predetermined desired value and to provide an output signal indicative of said change in heating current flow to said thermistor;

a reference circuit comprising a monitoring element exposed for heat contact with said desired liquid, said monitoring element having an electrical characteristic that changes as a single-valued function of temperature, an electronic circuit to control the flow of heating current to said monitoring element to establish the temperature of said monitoring element at a value substantially above ambient temperature, said circuit including reference means representing a predetermined desired value for said electrical characteristic of said monitoring element and being adapted, upon change in the actual value of said electrical characteristic of said monitoring element, to change said heating current flow to said monitoring element to restore the value of said characteristic toward said predetermined desired value and to provide an output signal indicative of said change in heating current flow to said monitoring element; and an alien liquid indicator circuit responsive to the difference between the output signal of said detection circuit and the output signal of said reference circuit for indicating the presence of said alien liquid.

17. An oil detector comprising the detector of claim 16 wherein the reference monitoring element is exposed to water and said thermistor is exposed to fluid which may be oil or water.

18. The detector of claims 1, 2, 6, 9, 13 or 16 wherein said alien fluid to be sensed is floating on water, characterized in that said monitoring element has an electrical resistance decreasing with increasing temperature, whereby the heating effect of said monitoring element, when said floating liquid has lower viscosity than water, is less than when water is present, thereby enabling reduced convection losses in the presence of high oil distillates and the like to enable detection thereof.

* * * * *